United States Patent [19]

Ogura et al.

[11] Patent Number: 5,198,450
[45] Date of Patent: Mar. 30, 1993

[54] PHENYLALKANOYLAMINE DERIVATIVES, PROCESS FOR PREPARING THE SAME, AND USAGE OF THE SAME

[75] Inventors: Kuniyoshi Ogura; Tomoji Aotsuka; Motoki Torizuka; Mitsuo Soeda; Yoshiaki Tanaka; Hisayoshi Kato; Naoyoshi Miura; Naoki Nakata; Hikaru Morita; Akihiro Okubo, all of Konan, Japan

[73] Assignee: Zeria Pharmaceutical Co., Ltd., Tokyo, Japan

[21] Appl. No.: 601,795

[22] PCT Filed: May 1, 1989

[86] PCT No.: PCT/JP89/00461

§ 371 Date: Jan. 7, 1991

§ 102(e) Date: Jan. 7, 1991

[87] PCT Pub. No.: WO89/10918

PCT Pub. Date: Nov. 16, 1989

[30] Foreign Application Priority Data

May 9, 1988 [JP] Japan .................. 63-112067
Mar. 13, 1989 [JP] Japan .................. 1-57865

[51] Int. Cl.$^5$ .................. A61K 31/40; A61K 31/41; C07D 277/04; C07D 207/04
[52] U.S. Cl. .................. 514/326; 514/365; 514/422; 514/423; 544/132; 544/133; 546/208; 546/209; 548/200; 548/518; 548/540
[58] Field of Search .................. 548/200, 540, 518; 514/365, 326, 423, 422; 544/132, 133; 546/208, 209

[56] References Cited

FOREIGN PATENT DOCUMENTS 0303434 2/1989 European Pat. Off.
2021445 12/1970 Fed. Rep. of Germany.
1336388 8/1963 France.
2043467 3/1971 France.

OTHER PUBLICATIONS

Mukaiyama et al., (Chemical Abstract), 92(1), 1979, #6522t.
Mukaiyama et al., (Chemical Abstract), 91(23), 1979, #192996c.
Chemical Abstracts, 63:9885h (1965) (Michael Sy & Georges Andre Thiault), Bull. Soc. Chim. France, 1965 (5), 1309-1315 (Fr).
Chemical Abstracts, 82, 1, 82(1):3917h, (1975), (Cont. Rech. Clin-Midy, Montpellier, Fr.), Krausj. F., et al., Arjneim.—Forsch. 1974, 24(9a), 1360-1364 (Fr.).

Primary Examiner—Mukund J. Shah
Assistant Examiner—Y. N. Gupta
Attorney, Agent, or Firm—Oblon, Spivak, McClelland, Maier & Neustadt

[57] ABSTRACT

An agent for treating or preventing cerebral circulation disorder, cerebral metabolism disorder, or memory disturbance is disclosed. The agent comprises as an effective component a phenylalkanoylamine derivative represented by the following formula (I),

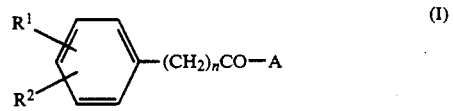

wherein A represents a 1,3-thiazolidin-3-yl group, a 1,2,3,6-tetrahydropyridin-1-yl group, a morpholino group, a thiomorpholin-4-yl group, or a 3-pyrrolin-1-yl group, $R^1$ and $R^2$, which may be the same or different, represent a hydrogen atom, a halogen atom, a lower alkyl group, a lower alkoxy group, a nitro group, an amino group, a guanidino group, or a group

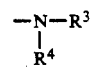

(wherein $R^3$ and $R^4$ independently represent a lower alkyl group or form in combination 5- or 6-membered heterocyclic group), and n represents an integer of 2-6, or a salt thereof. This agent is effective for treating or preventing cerebral hemorrhage sequela, cerebral infarction sequela, cerebral arteriosclesois, subarachnoid hemorrhage sequela, cranial injury sequela, cerebral operation sequela, cerebrovascular dementia, Parkinson's disease, Alzheimer's disease, Pick's disease, various anoxia toxicosis including, but not limited to anthracemia sequela, cerebral alcoholism related diseases, and the like.

1 Claim, No Drawings

PHENYLALKANOYLAMINE DERIVATIVES, PROCESS FOR PREPARING THE SAME, AND USAGE OF THE SAME

FIELD OF THE INVENTION

This invention relates to novel phenylalkanoylamine derivatives which are useful as medicines for treating or preventing cerebral circulation disorder, cerebral metabolism disorder, and memory disturbance, and to a process for preparing the same.

DESCRIPTION OF THE BACKGROUND ART

Senile dementia caused by such cerebral disorders as cerebrovascular disorder, cerebral circulation disorder, cerebral metabolism disorder, and memory disturbance has become a social problem in the society with prolonged life-span. A number of drugs for the treatment or prevention of these diseases, including cerebral vasodilators, cerebral metabolism accelerators, and the like, are clinically used.

None of these medicines, however, exhibit sufficient effects on the treatment of diseases such as cerebrovascular disorder sequelae, or the like.

Cerebral tissues of mammals rely upon aerobic glycolysis for the energy to maintain their functional activity. For this reason, a constant supply of a large amount of oxygen and glucose to brain tissues is necessary. It is a clinical knowledge that a decreased oxygen supply to brain tissues caused by circulation disorder, or the like remarkably lowers the brain cell functions. The continued decrease in oxygen supply to brain tissues extremely lowers brain cell functions. Interruption of oxygen supply (for several minutes) is known to completely inactivate physiological functions of brain cells and to cause irreversible organic disorders [J. Cereb. Blood Flow Metab. 9, 2–19, (1989]. In view of this, pharmacological experiments using hypoxia induction methods have long been carried out. A great attention to the problems concerning cerebral ischemia in recent years has led to the investigations about the cause of cerebral functional disorder or cerebral tissue disorder. The studies involving biochemistry, blood circulation dynamics, and electrophysiology resulted in the evidenced utility of hypoxia induction methods [Arch. Int. Pharmacodyn. 286, 299–307 (1987)]. Drugs protecting the brain from the induced hypoxia have been recognized as possessing more excellent effects on the improvement in cerebral circulation and cerebral metabolism, as well as on the prevention of amnesia than conventional drugs for improving cerebral circulation.

In view of this situation, the present inventors have undertaken extensive studies in order to develop a more excellent medicine for improving cerebral circulation and metabolism as well as for preventing amnesia. As a result, the inventors have found that phenylalkanoylamine derivatives represented by the following formula (I) exhibited excellent anti-hypoxic and anti-amnesic activities, and are pharmacologically useful. Such findings have led to the completion of this invention.

DISCLOSURE OF THE INVENTION

An object of this invention is to provide an agent for treating or preventing cerebral circulation disorder, cerebral metabolism disorder, or memory disturbance comprising as an effective component a phenylalkanoylamine derivative represented by the following formula (I),

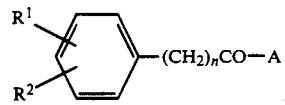

wherein A represents a 1,3-thiazolidin-3-yl group, a 1,2,3,6-tetrahydropyridin-1-yl group, a morpholino group, a thiomorpholin-4-yl group, or a 3-pyrrolin-1-yl group, $R^1$ and $R^2$, which may be the same or different, represent a hydrogen atom, a halogen atom, a lower alkyl group, a lower alkoxy group, a nitro group, an amino group, or a guanidino group, or a group

(wherein $R^3$ and $R^4$ independently represent a lower alkyl group or form in combination 5- or 6-membered heterocyclic group), and n represents an integer of 2-6, or a salt thereof.

Among the compounds represented by the formula (I) those represented by the following formula (I') are novel compounds. Accordingly, it is another object of this invention to provide phenylalkanoylamine derivatives represented by the following formula (I'),

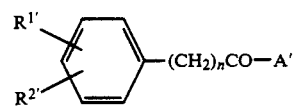

wherein A' represents a 1,3-thiazolidin-3-yl group, a 1,2,3,6-tetrahydropyridin-1-yl group, a morpholino group, a thiomorpholin-4-yl group, or a 3-pyrrolin-1-yl group, $R^{1'}$ and $R^{2'}$, which may be the same or different, represent a hydrogen atom, a halogen atom, a lower alkyl group, a lower alkoxy group, a nitro group, an amino group, a guanidino group, or a group

(wherein $R^3$ and $R^4$ independently represent a lower alkyl group or form in combination 5- or 6-membered heterocyclic group), and n represents an integer of 2-6, provided that when A' is a morpholino group, $R^{1'}$ and $R^{2'}$ can not be a hydrogen atom at the same time, and when A' is a thiomorpholin-4-yl group, $R^{1'}$ is not a fluorine atom and $R^{2'}$ is not a hydrogen atom, or a salt thereof, and a process for the preparation thereof.

BEST MODE FOR CARRING OUT THE INVENTION

Specific halogens which can be $R^1$, $R^2$, $R^{1'}$, or $R^{2'}$ in formulae (I) and (I') include, chlorine, fluorine, bromine, and the like. Chlorine and fluorine are especially preferable. Lower alkyl groups which can be $R^1$, $R^2$, $R^{1'}$, or $R^{2'}$ are linear or branched alkyl groups having 1–6 carbon atoms. Specific examples are methyl, ethyl, n-propyl, n-butyl, n-pentyl, n-hexyl, isopropyl, isobutyl, and t-butyl groups. A lower alkoxy groups are those having 1–6 carbon atoms such as methoxy, ethoxy, propyloxy, isopropyloxy, and pentyloxy group. Given as heterocyclic groups formed by $R^3$ and $R^4$ of the formula

are piperidino, morphorino, and pyrrolidin-1-yl groups, and the like. n represents an integer of 2-6, with especially preferable range being 3-5.

Following compounds are given as typical phenylalkanoylamine derivatives represented by the formula (I):

N-(4-phenylbutanoyl)thiazolidine
N-(4-phenylbutanoyl)-1,2,3,6-tetrahydropyridine
N-[4-(4-fluorophenyl)butanoyl]-1,2,3,6-tetrahydropyridine
N-[4-(4-methoxyphenyl)butanoyl]-1,2,3,6-tetrahydropyridine
N-[4-(4-chlorophenyl)butanoyl]-1,2,3,6-tetrahydropyridine
N-(5-phenylpentanoyl)-1,2,3,6-tetrahydropyridine
N-(6-phenylhexanoyl)thiazolidine
N-(7-phenylheptanoyl)thiazolidine
N-[4-(4-chlorophenyl)butanoyl]thiazolidine
N-[4-(4-fluorophenyl)butanoyl]thiazolidine
N-[4-(4-methoxyphenyl)butanoyl]thiazolidine
N-(5-phenylpentanoyl)thiazolidine
N-(3-phenylpropanoyl)thiazolidine
N-(6-phenylhexanoyl)-1,2,3,6-tetrahydropyridine
N-[6-(4-fluorophenyl)hexanoyl]thiazolidine
N-[5-(4-fluorophenyl)pentanoyl]-1,2,3,6-tetrahydropyridine
N-[7-(4-fluorophenyl)heptanoyl]-1,2,3,6-tetrahydropyridine
N-[3-(4-chlorophenyl)propanoyl]thiazolidine
N-[5-(4-chlorophenyl)pentanoyl]thiazolidine
N-[3-(4-chlorophenyl)propanoyl]-1,2,3,6-tetrahydropyridine
N-[6-(4-chlorophenyl-)hexanoyl]-1,2,3,6-tetrahydropyridine
N-[4-(4-tolyl)butanoyl]thiazolidine
N-[5-(4-tolyl)pentanoyl]thiazolidine
N-[7-(4-tolyl)heptanoyl]thiazolidine
N-[3-(4-tolyl)propanoyl]-1,2,3,6-tetrahydropyridine
N-[4-(4-tolyl)butanoyl]-1,2,3,6-tetrahydropyridine
N-[3-(4-methoxyphenyl)propanoyl]thiazolidine
N-[7-(4-methoxyphenyl)heptanoyl]thiazolidine
N-[3-(4-methoxyphenyl)propanoyl]-1,2,3,6-tetrahydropyridine
N-[7-(4-methoxyphenyl)heptanoyl]-1,2,3,6-tetrahydropyridine
N-(7-phenylheptanoyl)morpholine
N-(5-phenylpentanoyl)thiomorpholine
N-(5-phenylpentanoyl)-3-pyrroline
N-[4-(4-fluorophenyl)butanoyl]morpholine
N-[4-(4-fluorophenyl)butanoyl]-3-pyrroline
N-[3-(4-chlorophenyl)propanoyl]morpholine
N-[4-(4-chlorophenyl)butanoyl]morpholine
N-[3-(4-chlorophenyl)propanoyl]thiomorpholine
N-[4-(4-chlorophenyl)butanoyl]thiomorpholine
N-[7-(4-chlorophenyl)heptanoyl]-3-pyrroline
N-[6-(4-bromophenyl)hexanoyl]thiomorpholine
N-[5-(4-tolyl)pentanoyl]morpholine
N-[4-(4-tolyl)butanoyl]thiomorpholine
N-[4-(4-tolyl)butanoyl]-3-pyrroline
N-[4-(2,4-dichlorophenyl)butanoyl]morpholine
N-[5-(2,4-dichlorophenyl)pentanoyl]thiomorpholine
N-[6-(4-nitrophenyl)hexanoyl]morpholine
N-[3-(4-nitrophenyl)propanoyl]-3-pyrroline
N-[4-(4-aminophenyl)butanoyl]morpholine
N-[4-(4-aminophenyl)butanoyl]thiomorpholine
N-[3-(4-aminophenyl)propanoyl]thiomorpholine
N-[4-(4-aminophenyl)butanoyl]-3-pyrroline
N-[4-(4-methoxyphenyl)butanoyl]thiomorpholine
N-[5-(4-methoxyphenyl)pentanoyl]-3-pyrroline
N-[5-(2,4-dichlorophenyl)pentanoyl]thiazolidine
N-[5-(4-aminophenyl)pentanoyl]-1,2,3,6-tetrahydropyridine
N-[3-(4-aminophenyl)propanoyl]thiazolidine
N-[5-(4-methoxyphenyl)pentanoyl]-1,2,3,6-tetrahydropyridine
N-[4-(4-bromophenyl)butanoyl]thiazolidine
N-(4-phenylbutanoyl)thiomorpholine
N-(4-phenylbutanoyl)-3-pyrroline
N-[4-(2,4-dichlorophenyl)butanoyl]-1,2,3,6-tetrahydropyridine
N-[4-(4-nitrophenyl)butanoyl]-1,2,3,6-tetrahydropyridine
N-[4-(4-nitrophenyl)butanoyl]thiazolidine
N-[4-(4-aminophenyl)butanoyl]-1,2,3,6-tetrahydropyridine
N-[4-(4-aminophenyl)butanoyl]thiazolidine
N-[4-(4-aminophenyl)butanoyl]thiazolidine hydrochloride
N-[4-(2-amino-4-chlorophenyl)butanoyl]-3-pyrroline
N-[4-(2-amino-4-bromophenyl)butanoyl]morpholine
N-[4-bromo-2-chlorophenyl)butanoyl]-3-pyrroline
N-[4-(2-chloro-4-nitrophenyl)butanoyl]thiomorpholine
N-[4-(2-amino-4-methoxyphenyl)butanoyl]morpholine
N-[4-(4-methoxy-2-nitrophenyl)butanoyl]thiomorpholine
N-[4-(2-methoxy-4-nitrophenyl)butanoyl]-1,2,3,6-tetrahydropyridine
N-[5-(4-amino-2-chlorophenyl)pentanoyl]thiazolidine
N-[3-(2-chloro-4-methoxyphenyl)propanoyl]-1,2,3,6-tetrahydropyridine
N-[6-(2-amino-4-methoxyphenyl)hexanoyl]thiazolidine
N-[4-(4-guanidinophenyl)butanoyl]thiazolidine
N-[4-(4-guanidinophenyl)butanoyl]thiazolidine hydrochloride
N-[4-(4-dimethylaminophenyl)butanoyl]thiazolidine
N-[4-(4-dimethylaminophenyl)butanoyl]thiazolidine hydrochloride
N-[5-(4-guanidinophenyl)pentanoyl]thiazolidine
N-[6-(4-dimethylaminophenyl)hexanoyl]thiazolidine
N-[4-(4-guanidinophenyl)butanoyl]-1,2,3,6-tetrahydropyridine
N-[4-(4-dimethylaminophenyl)butanoyl]-1,2,3,6-tetrahydropyridine
N-[5-(4-guanidinophenyl)pentanoyl]morphorine
N-[3-(4-dimethylaminophenyl)propanoyl]morphorine
N-[3-(4-guanidinophenyl)propanoyl]thiomorphorine
N-[6-(4-dimethylaminophenyl)hexanoyl]thiomorphorine
N-[6-(4-guanidinophenyl)hexanoyl]-3-pyrroline
N-[4-(4-dimethylaminophenyl)butanoyl]-3-pyrroline
N-[4-(4-guanidinophenyl)butanoyl]thiazolidine sulfate
N-[4-(4-diethylaminophenyl)butanoyl]thiazolidine
N-[4-(4-piperidinophenyl)butanoyl]thiazolidine
N-[4-(4-morphorinophenyl)butanoyl]thiazolidine
N-[4-(4-guanidinophenyl)butanoyl]thiazolidine carbonate Depending on the type of group $R^1$ or $R^2$, compounds of formula (I) may form an acid addition salt. Any pharmaceutically acceptable acid can be used for forming the salt, including, for example, an inorganic acid such as hydrochloric acid, sulfuric acid, carboxylic acid, and the like; an organic acid such as formic acid, citric acid, and the like; a sulfonic acid such as methanesulfonic acid, benzenesulfonic acid.

The compounds of formula (I) can be prepared, for example, by reacting a phenylalkanoic acid or an active derivative thereof of the following formula (II),

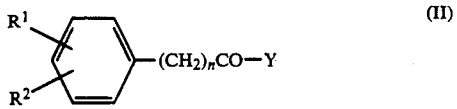

(II)

(wherein Y represents a halogen atom, an active ester residual group, or a hydroxy group, and $R^1$, $R^2$, and n have the same meanings as previously defined) with 1,3-thiazolidine, 1,2,3,6-tetrahydropyridine, morpholine, thiomorpholine, or 3-pyrroline.

A preferable active derivative of a phenylalkanoic acid (II) is an acid halide such as acid chloride, acid bromide, or the like, or an active ester such as N-hydroxysuccinimide ester, and the like.

The reaction using reactive derivative of phenylalkanoic acid as a starting material is carried out in an inert solvent in the presence or absence of a basic compound at $-40°$ to $200°$ C., at $-4°$ to $50°$ C., in particular. Any inert solvents which do not have a detrimental effect on the reaction may be used. Preferable inert solvents are water, ethers (e.g. diethyl ether, tetrahydrofuran, dioxane, etc.), halides (e.g. dichloromethane, dicloroethane, chloroform, carbon tetrachloride, etc.), and hydrocarbon (e.g. benzene, toluene, etc.). Basic compounds which can be used include alkali metal hydroxides, alkali metal carbonates, trialkyl amines, aromatic amines, and the like.

The reaction using a phenylalkanoic acid (II) is preferably carried out in the presence of a condensing agent in an inert solvent. Any aprotonic solvent can be used in this reaction. Preferable examples of such aprotonic solvent include halides (e.g. dichloromethane, dichloroethane, chloroform, carbon tetrachloride, etc.), ethers (e.g. diethyl ether, tetrahydrofuran, dioxane, etc.), and the like. Condensing agents which are commonly used for this type of reaction can be used in this reaction. Preferable examples are carbodiimides such as N-ethyl-N'-(3-dimethylaminopropyl)carbodiimide or its hydrochloride, N,N'-dicyclohexylcarbodiimide, and the like. The reaction temperature of $-20°$ to $100°$ C. is preferable.

Among the compounds of formula (I), those having an amino group for $R^1$ or $R^2$ can also be prepared by reducing a compound having a nitro group for $R^1$ or $R^2$. The reduction can be performed either catalytically or by using a metal. The metallic reduction is preferably carried out by using tin or zinc under acidic conditions.

A compound having guanidino group for $R^1$ or $R^2$ can also be prepared by reacting a compound of formula (I) having a amino group for $R^1$ or $R^2$ with cyanamid, O-alkyl urea, or O-alkyl thiourea. A compound of formula (I) having a dialkylamino group for $R^1$ or $R^2$ can be prepared by the reaction of the above compound having amino group for $R^1$ or $R^2$ and an alkylating agent. Alkylating agents which can be used include trialakyl phosphate such as trimethyl phosphate, triethyl phosphate; dialkyl sulfate such as dimethyl sulfate, diethyl sulfate; and the like.

The compounds of formula (I) thus prepared, exhibit excellent anti-hypoxic and anti-amnesic activities, and are safe, and are thus pharmacologically useful as a medicine for treating or preventing cerebral circulation disorder, cerebral metabolism disorder, or memory disturbance. Such a medicine may consist only of a compound of formula (I) or may comprise, in addition to a compound of formula (I), any pharmaceutically active components. It can be prepared into various dosing forms for oral or non-oral administration by formulating together with various pharmacologically acceptable carriers.

When this compound is prepared for oral administration, it is appropriately formulated together with suitable additives, including excipients such as lactose, mannitol, corn starch, crystallized cellulose, etc., binders such as cellulose derivatives, gum arabic, gelatin, etc., disintegrators such as calcium carboxymethyl cellulose, etc., lubricants such as talc, magnesium stearate, etc., and the like. These may be formed into tablets, granules, powders, or capsules. These solid formulations can also be prepared into enteric coated pills using a coating substrate such as hydroxypropylmethyl cellulose phthalate, hydroxypropylmethyl cellulose acetate succinate, cellulose acetate phthalate, methacrylate copolymer, or the like. It can also be made into a soft capsular preparation, in which the compound of formula (I) is dissolved in a medium-chain fatty acid triglyceride, safflower oil, soy been oil, polyethylene glycol 400, or the like. Non-oral dosing forms include an injection, into which water, ethanol, glycerol, conventional surface active agents, and the like may be formulated. The compound of formula (I) can also be prepared in a suppository using a suitable suppository substrate.

Although a dose of the compound of formula (I) administered may vary depending on the body weight, age, and symptoms of the subject, the intended treatment effect, the manner by which it is administered, and the period of administration, a generally appropriate amount may be from 1 to 2,000 mg per day, preferably from 10 to 200 mg per day, with the frequency of administration being 1 to 3 times per day.

EXAMPLES

The present invention is hereinafter described more specifically by way of examples, which shall not be construed as limiting the present invention.

EXAMPLE 1

N-(4-phenylbutanoyl)-1,2,3,6-tetrahydropyridine

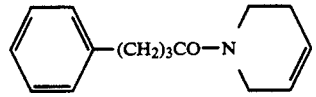

5 mmol of 4-phenyl butyric acid, 5 mmol of 1,2,3,6-tetrahydropyridine, and 6 mmol of 1-ethyl-3-(3-dimethylaminopropyl)carbodiimide hydrochloride were mixed with 20 ml of methylene chloride. The mixture was reacted for 2 hours at room temperature with stirring. The reaction mixture was washed with 5% hydrochloric acid, 2% sodium hydroxide, and brine. The organic layer was dried over anhydrous sodium sulfate. The solvent was evaporated under reduced pressure and the residue was purified by column chromatography on silica gel to obtain 950 mg of colorless crystals of N-(4-phenylbutanoyl)-1,2,3,6-tetrahydropyridine (yield: 83%).

mp: below 30° C.

IR (neat) cm$^{-1}$: 2850-3100, 1645, 1435, 1240, 745, 700

NMR (CDCl$_3$) δ: 1.43-2.50 (6H, m), 2.64 (2H, t, J=7 Hz), 3.21-4.18 (4H, m), 5.21-6.16 (4H, m), 7.11-7.32 (5H, m)

EXAMPLES 2-14

Compounds listed in Tables 1 and 2 were prepared in the same manner as in Example 1.

TABLE 1

R$^1$—C$_6$H$_3$(R$^2$)—(CH$_2$)$_n$CO—N⟨tetrahydropyridine⟩

| Example No. | R$^1$ | R$^2$ | n | m.p. (C.°) | IR(cm$^{-1}$) | NMR(CDCl$_3$)δ |
|---|---|---|---|---|---|---|
| 2 | H | 4-F | 3 | 35-36 | (KBr) 2920, 2840 1625, 1505 1435, 1215 | 1.40-2.90(8H, m) 3.10-4.27(4H, m) 5.30-6.03(2H, m) 6.60-7.74(4H, m) |
| 3 | H | 4-OCH$_3$ | 3 | Oil | (neat) 2940, 1710 1640, 1515 1440, 1250 1035 | 1.70-2.40(6H, m) 2.63(2H, t, J=7Hz) 3.23-4.13(4H, m) 3.77(3H, s) 5.37-6.10(2H, m) 6.70-7.23(4H, m) 6.96-7.44(4H, m) |
| 4 | H | 4-Cl | 3 | 38 | (neat) 2830-3030 1630, 1495 1435, 810 | 1.48-2.60(6H, m) 2.63(2H, t, J=7Hz) 3.24-4.21(4H, m) 5.34-6.06(2H, m) |
| 5 | H | H | 4 | Oil | (neat) 2925, 2850 1635, 1430 | 1.20-2.90(10H, m) 3.13-4.70(4H, m) 5.23-6.13(2H, m) 7.12(5H, s) |
| 6 | H | 4-NO$_2$ | 3 | Oil | (neat) 2925, 1635 1515, 1340 | 1.37-4.27(2H, m) 5.37-6.10(2H, m) 7.10-8.27(4H, m) |
| 7 | H | H | 5 | Oil | (neat) 2940, 2850 1625, 1430 | 1.10-4.20(16H, m) 5.37-6.07(2H, m) 7.13(5H, s) |
| 8 | 2-Cl | 4-Cl | 3 | Oil | (neat) 2925, 1625 1440, 1240 745 | 1.53-2.97(8H, m) 3.30-4.20(4H, m) 5.33-6.13(2H, m) 7.10-7.57(3H, m) |

TABLE 2

R$^1$—C$_6$H$_3$(R$^2$)—(CH$_2$)$_n$CO—N⟨S-heterocycle⟩

| Example No. | R$^1$ | R$^2$ | n | m.p. (C.°) | IR(cm$^{-1}$) | NMR(CDCl$_3$)δ |
|---|---|---|---|---|---|---|
| 9 | H | 4-Cl | 3 | 51.5-52.5 | (KBr) 2880-2940 1645, 1490 1415, 835 | 1.73-2.50(4H, m) 2.66(2H, t, J=7Hz) 2.80-3.24(2H, m) 3.44-4.02(2H, m) 4.20-4.73(2H, m) 6.96-7.43(4H, m) |
| 10 | H | 4-F | 3 | Oil | (neat) 2875-2940 1640, 1510 1415, 1215 | 1.47-3.27(8H, m) 3.33-4.00(2H, m) 4.20-4.87(2H, m) 6.67-7.33(4H, m) |
| 11 | H | 4-OCH$_3$ | 3 | 67-68 | (KBr) 2960, 1635 1605, 1510 1410, 1240 1035 | 1.83-3.20(8H, m) 3.47-4.00(2H, m) 3.77(3H, s) 4.33-4.67(2H, m) 6.80(2H, d) 7.10(2H, d) |
| 12 | H | H | 4 | Oil | (neat) 2970, 1650 1500, 1420 1265, 1190 | 1.53-1.87(5H, m) 2.13-3.20(6H, m) 3.50-4.00(2H, m) 4.33-4.67(2H, m) |

TABLE 2-continued

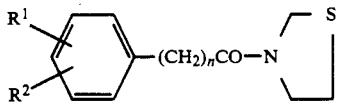

| Example No. | Compounds R¹ | R² | n | m.p. (C.°) | IR(cm⁻¹) | NMR(CDCl₃)δ |
|---|---|---|---|---|---|---|
| 13 | H | H | 2 | Oil | (neat) 2940, 1650 1495, 1420 1260, 1185 | 7.17(5H, s) 2.40–3.27(6H, m) 3.43–4.00(2H, m) 4.27–4.67(2H, m) |
| 14 | H | 4-NO₂ | 3 | 69 | (KBr) 2950, 1630 1600, 1510 1425, 1340 850 | 7.20(5H, s) 1.57–3.33(8H, m) 3.43–3.90(2H, m) 4.53(2H, d, J=7Hz) 7.17–8.37(4H, m) |

EXAMPLE 15

N-(4-phenylbutanoyl)thiazolidine

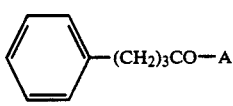

5.5 mmol of thiazolidine and 5.5 mmol of triethylamine were dissolved in 10 ml of methylene chloride. To the solution 5 mmol of 4-phenylbutanoyl chloride was added dropwise under ice-cooling with stirring. The mixture was left to raise to room temperature and further heated under refluxing for 2 hours. The resulting reaction mixture was washed with 1N hydrochloric acid, brine, and saturated aqueous solution of sodium chloride, and dried over anhydrous sodium sulfate. The solvent was evaporated by distillation and the residue was purified by column chromatography on silica gel to obtain 1.14 g of colorless crystals of N-(4-phenylbutanoyl)thiazolidine (yield: 88%).

mp: below 30° C.

IR (neat) cm⁻¹: 2880–3100, 1645, 1415, 750, 700

NMR (CDCl₃) δ: 1.64–2.49 (4H, m), 2.66 (2H, t, J=7 Hz), 2.80–3.14 (2H, m), 3.38–3.97 (2H, m), 4.21–4.67 (2H, m), 7.16 (5H, s)

EXAMPLES 16–18

Compounds listed in Table 3 were prepared in the same manner as in Example 15

TABLE 3

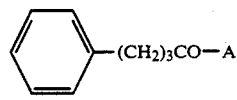

| Example No. | Compounds R¹ R² | n | m.p. (C.°) | IR(cm⁻¹) | NMR(CDCl₃)δ |
|---|---|---|---|---|---|
| 16 | —N◯O | | Oil | (neat) 2860, 1650 1450, 1430 1270, 1115 | 1.77–2.87(6H, m) 3.17–3.90(8H, m) 7.20(5H, s) |

TABLE 3-continued

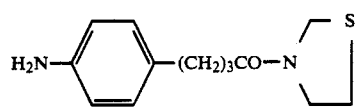

| Example No. | Compounds R¹ R² | n | m.p. (C.°) | IR(cm⁻¹) | NMR(CDCl₃)δ |
|---|---|---|---|---|---|
| 17 | —N◯S | | Oil | (neat) 2920, 1650 1450, 1420 1290, 1190 | 1.90–2.87(10H, m) 3.47–4.00(4H, m) 7.15(5H, s) |
| 18 | —N◯ | | 37–38 | (KBr) 2850–2940 1635, 1615 1440, 995 | 1.63–2.93(6H, m) 3.90–4.40(4H, m) 5.57–6.00(2H, m) 7.17(5H, s) |

EXAMPLE 19

N-[4-(4-aminophenyl)butanoyl]thiazolidine

To a mixture of 9 ml of acetic acid, 6 ml of water, and 1.0 g of zinc powder was gradually added 2 mmol of N-[4-(4-nitrophenyl)butanoyl]thiazolidine at room temperature in small portions with stirring. After the addition, the mixture was stirred for 2 hours at the same temperature to complete the reaction. Zinc powder was removed by filtration. The filtrate was weakly alkalinized with 10% sodium hydroxide and extracted with ethyl acetate. The organic layer was dried over anhydrous sodium sulfate. The solvent was evaporated under reduced pressure and the residue was purified by column chromatography on silica gel to obtain 335 mg of colorless crystals of N-[4-(4-aminophenyl)butanoyl]thiazolidine (yield: 67%).

mp: 80°–82° C.

IR (KBr) cm⁻¹: 3425, 3350, 2950, 1635, 1610, 1515, 1420, 1370, 1285, 1175, 810

NMR (CDCl₃) δ: 1.86–2.04 (2H, m), 2.22–2.37 (2H, m), 2.57 (2H, t, J=7 Hz), 2.90–3.10 (2H, m), 3.14–3.73

(2H, br), 3.62 (1H, t, J=6 Hz), 3.83 (1H, t, J=6 Hz), 4.37 (1H, s), 4.57 (1H, s), 6.61 (2H, d, J=8 Hz), 6.97 (2H, d, J=8 Hz)

EXAMPLE 20

N-[4-(4-aminophenyl)butanoyl]thiazolidine hydrochloride

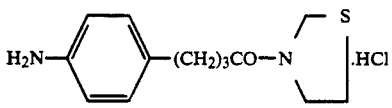

To 5 ml of alcoholic hydrogen chloride 1 mmol of N-[4-(4-aminophenyl)butanoyl]thiazolidine was added and dissolved under heating. The mixture was stirred at room temperature for 2 hours. After the reaction, the solvent was evaporated under reduced pressure. To the residue was added anhydrous ether and precipitates thus produced were collected by filtration to obtain 0.28 g of colorless crystals of N-[4-(4-aminophenyl)-butanoyl]thiazolidine hydrochloride (yield: 98%).

mp: 166°-169° C.

IR (KBr) cm$^{-1}$: 2850, 2590, 1665, 1610, 1515, 1450, 810

NMR (DMSO) δ: 1.60-1.91 (2H, m), 2.14-2.70 (4H, m), 2.96 (1H, t, J=6 Hz), 3.06 (1H, t, J=6 Hz), 3.49-3.75 (2H, m), 4.44 (1H, s), 4.51 (1H, s), 5.60-6.40 (3H, br), 7.13-7.48 (4H, m)

EXAMPLE 21

N-[4-(4-dimethylaminophenyl)butanoyl]thiazolidine

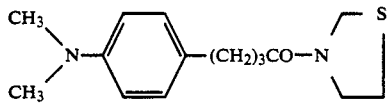

A mixture of 2 mmol of N-[4-(4-aminophenyl)-butanoyl]-thiazolidine prepared in Example 19 and 2 mmol of trimethyl phosphate was gradually heated in an argon atmosphere and stirred at 180° C. for 2 hours. After the mixture was allowed to cool, 2 ml of 15% NaOH was added to it. The reaction mixture was stirred for another 2 hours at room temperature and then extracted with methylene chloride. The residue was dried over anhydrous sodium sulfate, followed by evaporation of the solvent under reduced pressure. The residue was purified by silica gel column chromatography to obtain 93 mg of colorless crystals of N-[4-(4-dimethylaminophenyl)butanoyl]thiazolidine (yield: 17%).

mp: 54°-55° C.

IR (KBr) cm$^{-1}$: 2920, 1635, 1520, 1425, 1335

NMR (CDCl$_3$) δ: 1.91-2.20 (2H, m), 2.27-2.34 (2H, m), 2.59 (2H, t, J=8 Hz), 2.91 (6H, s), 2.90-3.06 (2H, m), 3.61-3.86 (2H, m), 4.38 (1H, s), 4.58 (1H, s), 6.70 (2H, d, J=8 Hz), 7.06 (2H, d, J=8 Hz)

EXAMPLE 22

N-[4-(4-guanidinophenyl)butanoyl]thiazolidine hydrochloride

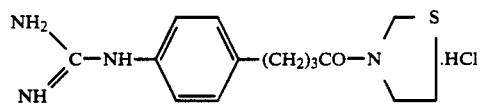

1 mmol of N-[4-(4-aminophenyl)butanoyl]thiazolidine hydrochloride prepared in Example 20 and 1 mmol of cyanamide were dissolved with 5 ml of anhydrous ethanol. The solution was stirred under heating at 70° C. for 4 hours. The reaction mixture was concentrated under reduced pressure to obtain a crystalline residue, which was recrystallized from an ethanol-ether mixed solvent to obtain 210 mg of colorless crystals of N-[4-(4-guanidinophenyl)butanoyl]thiazolidine hydrochloride (yield: 64%).

mp: 146°-148° C. (decomposed)

IR (KBr) cm$^{-1}$: 2830, 2520, 1605, 1510, 1450

NMR (DMSO-d$_6$) δ: 1.75-1.83 (2H, m), 2.30-2.38 (2H, m), 2.61 (2H, t, J=7 Hz), 2.94-3.09 (2H, m), 3.61-3.68 (2H, m), 4.43 (1H, s), 4.50 (1H, s), 7.27 (4H, s), 8.45-8.72 (5H, br)

Anti-hypoxic activity

Groups of ICR male mice (Charls River Co.), aged 4 to 5 weeks, each group consisting of 10 mice and each mouse having been fasted for 24 hours, were used for the test. Mice were placed in a colorless desiccator (diameter: 19 cm, height: 30 cm) made of synthetic resin and having 2 bulbs, one at the upper portion and the other at the lower portion, for replacing the gas therein. A mixed gas (4% O$_2$+96% N$_2$) was fed from the upper bulb at a rate of 10 l/min to measure the period of time until respiratory arrest took place for each mouse. The time measured was taken as the time of survival.

Each tested compound suspended in 5% gum arabic solution was intraperitoneally administered 30 minutes before the start of the mixed gas feeding. A group of mice to which only 5% gum arabic solution was intraperitoneally administered was used as a control.

Compounds, not sufficiently suspended in 5% gum arabic, were dissolved with Tween 80 and sesame oil so that the final concentrations of these materials were 1% and 3%, respectively, followed by the addition of 5% gum arabic. The anti-hypoxic activity was determined according to the following formula:

$$\text{Anti-hypoxic Activity (\%)} = \frac{\text{Survival time of the group to which a test compound was administered}}{\text{Survival time of the control group}} \times 100$$

The results are shown in Table 4.

TABLE 4

| Tested Compounds | Dose (mg/kg) | Activity (%) |
|---|---|---|
| Control | — | 100 |
| Compound of Ex. 1 | 100 | 221 |
| Compound of Ex. 2 | 100 | 200 |
| Compound of Ex. 5 | 100 | 282 |
| Compound of Ex. 15 | 100 | 227 |
| Compound of Ex. 16 | 100 | 151 |
| Compound of Ex. 19 | 100 | 219 |
| Compound of Ex. 20 | 100 | 216 |

TABLE 4-continued

| Tested Compounds | Dose (mg/kg) | Activity (%) |
|---|---|---|
| Aniracetam | 100 | 115 |
| Aniracetam | 300 | 134 |
| Calcium hopantenate | 250 | 135 |
| Idebenone | 100 | 140 |

Anti-amnesic activity

Compounds of this invention were checked with respect to their abilities to prevent the inhibition of long-term memory fixation by electric convulsion shock (ECS). CD female rats (Charls River Co.), weighed 60–80 g were used for the test. One hour after the administration of a compound of this invention, the acquisition trial according to the passive avoidance training was performed on the rats. A foot shock was given to the rats when they entered into a dark room. Immediately after that an amnesic treatment by ECS or a sham amnesic treatment was performed. Twenty four (24) hours after the acquisition trials the retention trial was performed. Latency to entering into a dark room was measured. The results are shown in Table 5.

TABLE 5

| Tested Substance (P.O.) | Amnesic Treatment | Latency to entering into a dark room (sec) |
|---|---|---|
| Solvent | Sham Treatment | 142.4 |
| Solvent | ECS | 1.5 |
| Compound of Ex. 1 (300 mg/kg) | ECS | 62.7 |
| Compound of Ex. 15 (300 mg/kg) | ECS | 69.1 |

Toxicity Experiment

Intraperitoneal administration

Groups of ICR male mice, aged 4 to 5 weeks, each group consisting of 10 mice, were used for the test. A dose of 300 mg/kg of each compound prepared in Examples 1–20 suspended in 5% gum arabic was intraperitoneally administered to each group of mice. No fatal problem in mice was observed during a period of 7 days.

Oral administration

Groups of Fisher 344 male rats, aged 6 weeks, each group consisting of 5 rats, were used for the test. A dose of 200, 400, or 800 mg/kg of each of the compounds prepared in the Examples, each suspended with 10% gum arabic, was orally administered to each group of rats. No fatal problem due to the toxicity of the compounds of this invention was observed.

Preparation Example 1

| Compound of Example 1 | 20 g |
|---|---|
| Lactose | 315 g |
| Corn starch | 125 g |
| Crystallized cellulose | 25 g |

The above components were blended to obtain a homogeneous mixture. After the addition of 200 ml of 7.5% hydroxypropyl cellulose, the mixture was made into granule by means of an extruding granulator using a screen with a 0.5 mm diameter. The granule was rounded and dried to produce a granulous preparation. The dried granule was coated with 1.9 kg of a film-coating liquid having the following composition using a fluid-type granulator to produce enteric coated granules.

| Hydroxypropylmethyl cellulose phthalate | 5.0 wt % |
|---|---|
| Stearic acid | 0.25 wt % |
| Methylene chloride | 50.0 wt % |
| Ethanol | 44.75 wt % |

Preparation Example 2

| Compound of Example 15 | 20 g |
|---|---|
| Lactose | 100 g |
| Corn starch | 36 g |
| Crystallized cellulose | 30 g |
| Calcium carboxymethyl cellulose | 10 g |
| Magnesium stearate | 4 g |

The above components were homogeneously mixed and prepared in tablets each weighing 200 mg by means of a one-shot tablet machine using a 7.5 mm screw.

Spray coating was applied to the tablets to prepare enteric film-coated tablets having the film weight of 10 mg per tablet. The composition of the coating liquid was as follows:

| Hydroxypropylmethyl cellulose phthalate | 8.0 wt % |
|---|---|
| Glycerine fatty acid ester (Myvacet, trade name) | 0.4 wt % |
| Methylene chloride | 50.0 wt % |
| Breached beeswax | 0.1 wt % |
| Isopropanol | 41.5 wt % |

Preparation Example 3

| Compound of Example 5 | 200 g |
|---|---|
| Polysorbate 80 | 20 g |
| Panasat | 1780 g |

The above components were mixed to dissolve each other. The solution was prepared into soft capsules, each containing 200 mg of the above medicinal liquid, using a film forming liquid containing 100 parts by weight of gelatin, 30% by weight of high concentration glycerol, 0.4% by weight of ethyl parabene, and 0.2% by weight of propyl parabene.

Preparation Example 4

| Compound of Example 19 | 100 mg |
|---|---|
| Sodium acetate | 2 mg |
| Acetic acid (for adjusting pH to 5.8) | Appropriate amount |
| Purified water | Balance |
| | Total 10 ml/vial |

The above components were prepared into an injection liquid according to a conventional method.

Industrial Applicability

As illustrated above, the compounds of this invention exhibit strong anti-amnesic and anti-hypoxic activities, and are highly safe. Thus, they are useful as medicines for treating or preventing cerebral circulation disorder, cerebral metabolism disorder, and memory disturbance.

More specific utilities of the medicine of this invention are for treating or preventing cerebral hemorrhage sequela, cerebral infarction sequela, cerebral arterioscleosis, subarachnoid hemorrhage sequela, cranial injury sequela, cerebral operation sequela, cerebrovascular dementia, Parkinson's disease, Alzheimer's disease, Pick's disease, various anoxia toxicosis including, but not limited to anthracemia sequela, cerebral alcoholism related diseases, and the like.

What is claimed is:

1. A pharmaceutical composition for treating or preventing cerebral circulation disorder, cerebral metabolism disorder, or memory disturbance comprising an effective component a pharmaceutically effective amount of a phenylalkanoylamine derivative represented by the following formula (I),

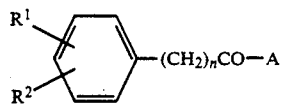

wherein A represents a 1,3-thiazolidin-3-yl group, or a 3-pyrrolin-1-yl group, $R^1$ and $R^2$, which may be the same or different, represent a hydrogen atom, a halogen atom, a lower alkyl group, a lower alkoxy group, a nitro group, an amino group, a guanidino group, or a group

(wherein $R^3$ and $R^4$ independently represent a lower alkyl group or form in combination 5- or 6-membered heterocyclic group selected from the group consisting of a piperidinyl moiety, and a pyrrolidinyl moiety), and n represents an integer of 2-6, or a salt thereof and a pharmaceutically acceptable carrier.

* * * * *